United States Patent
Weir et al.

(10) Patent No.: US 7,164,146 B2
(45) Date of Patent: Jan. 16, 2007

(54) SYSTEM FOR DETECTING STRUCTURAL DEFECTS AND FEATURES UTILIZING BLACKBODY SELF-ILLUMINATION

(75) Inventors: John Douglas Weir, Huntington, NY (US); Donald DiMarzio, Northport, NY (US); Steven Chu, Ronkonkoma, NY (US); Robert P. Silberstein, New York, NY (US)

(73) Assignee: Northrop Grumman Corporation, Los Angeles, CA (US)

( * ) Notice: Subject to any disclaimer, the term of this patent is extended or adjusted under 35 U.S.C. 154(b) by 279 days.

(21) Appl. No.: 10/971,217

(22) Filed: Oct. 22, 2004

(65) Prior Publication Data
US 2006/0086912 A1    Apr. 27, 2006

(51) Int. Cl.
*G01N 21/86* (2006.01)
(52) U.S. Cl. ............... 250/559.4; 250/559.27; 250/559.45
(58) Field of Classification Search ............. 250/559.4, 250/559.27, 559.45; 356/239.1, 239.2
See application file for complete search history.

(56) References Cited

U.S. PATENT DOCUMENTS

| | | | |
|---|---|---|---|
| 3,504,524 A | 4/1970 | Maley | |
| 3,973,122 A * | 8/1976 | Goldberg | 250/338.1 |
| 4,647,220 A | 3/1987 | Adams et al. | |
| 4,682,222 A | 7/1987 | Smith et al. | |
| 4,878,116 A | 10/1989 | Thomas et al. | |
| 4,988,875 A | 1/1991 | Ortiz et al. | |
| 5,065,630 A | 11/1991 | Hadcock et al. | |
| 5,258,705 A | 11/1993 | Okamoto et al. | |
| 5,287,183 A | 2/1994 | Thomas et al. | |
| 5,703,362 A | 12/1997 | Devitt et al. | |
| 5,763,786 A | 6/1998 | Camplin et al. | |
| 5,782,974 A | 7/1998 | Sorensen et al. | |
| 5,900,632 A | 5/1999 | Sterling et al. | |
| 5,963,653 A | 10/1999 | McNary et al. | |

(Continued)

FOREIGN PATENT DOCUMENTS

JP    11160264    6/1999

(Continued)

OTHER PUBLICATIONS

Leftwich et al., "Infrared Inspection of Multilayer Laminates and Composite Structures", IEEE Trans. on Indust. Electronics and Control Instr., vol. IECI-18, No. 2, May 1971.

*Primary Examiner*—Que T. Le
(74) *Attorney, Agent, or Firm*—Alan G. Towner, Esq.; Pietragallo, Bosick & Gordon LLP

(57) ABSTRACT

A system is disclosed which utilizes the substantially steady-state temperature of a coated object, in conjunction with an optical detection system, to selectively view defects and features of the object below the coating without the necessity of transient heating or IR illumination and reflectance imaging. The optical detector, such as an IR camera, may be tailored for the wavelengths at which the coating material is substantially transparent, thereby maximizing the viewing clarity of the defects and features under the coating, and distinguishing them from any spurious features on the top surface of the coating. The present system enables the inspection of small or large areas in real time, without requiring complex image acquisition, storage and image processing equipment and software.

39 Claims, 15 Drawing Sheets

U.S. PATENT DOCUMENTS

| | | |
|---|---|---|
| 6,000,844 A | 12/1999 | Cramer et al. |
| 6,012,840 A | 1/2000 | Small, IV et al. |
| 6,049,081 A | 4/2000 | Sterling et al. |
| 6,160,625 A | 12/2000 | Damer et al. |
| 6,184,528 B1 | 2/2001 | DiMarzio et al. |
| 6,269,179 B1 | 7/2001 | Vachtsevanos et al. |
| 6,399,949 B1 | 6/2002 | Roney, Jr. et al. |
| 6,452,180 B1 | 9/2002 | Nistler et al. |
| 6,471,396 B1 | 10/2002 | Biel |
| 6,489,992 B1 | 12/2002 | Savoye |
| 6,495,833 B1 | 12/2002 | Alfano et al. |
| 6,515,285 B1 | 2/2003 | Marshall et al. |
| 6,517,236 B1 | 2/2003 | Sun et al. |
| 6,517,238 B1 | 2/2003 | Sun et al. |
| 6,597,448 B1 | 7/2003 | Nishiyama et al. |
| 6,853,926 B1 | 2/2005 | Alfano et al. |
| 6,873,680 B1 | 3/2005 | Jones |
| 2002/0050566 A1 | 5/2002 | Nilsson et al. |
| 2004/0026622 A1 | 2/2004 | DiMarzio et al. |
| 2005/0031974 A1 | 2/2005 | Fukuhara |
| 2005/0056786 A1 | 3/2005 | Shepard et al. |
| 2005/0061247 A1 | 3/2005 | Shibata et al. |

FOREIGN PATENT DOCUMENTS

| | | |
|---|---|---|
| WO | WO 01/020319 | 3/2001 |

* cited by examiner

GRAPHITE PAINTED PANEL AT 89°F, RT-CALIBRATION

GRAPHITE PAINTED PANEL AT 90°F, 84°F HOT-CALIBRATION

GRAPHITE WITH Cu FIBER PAINTED PANEL AT 90°F,
84°F HOT-CALIBRATION

GRAPHITE WITH Cu FIBER PAINTED PANEL AT 74°F,
84°F HOT-CALIBRATION

GRAPHITE WITH Cu WEAVE, PAINTED PANEL AT 91°F,
RT-CALIBRATION

GRAPHITE WITH Cu WEAVE, PAINTED PANEL AT 87°F,
RT-CALIBRATION

GRAPHITE WITH Cu WEAVE, PAINTED PANEL AT 82°F,
RT-CALIBRATION

GRAPHITE, PAINTED PANEL AT 90°F, RT-CALIBRATION

GRAPHITE, PAINTED PANEL AT 86°F, RT-CALIBRATION

GRAPHITE, PAINTED PANEL AT 82°F, RT-CALIBRATION

GRAPHITE, PAINTED PANEL AT 78°F, RT-CALIBRATION

GRAPHITE, PAINTED AND PRIMED PANEL: VISIBLE IMAGE

GRAPHITE WITH Cu WEAVE, PAINTED AND PRIMED PANEL:
VISIBLE IMAGE

ALUMINUM C2: VISIBLE IMAGE

ALUMINUM C2 1x MAG. AT 77°F, IR REFLECTANCE IMAGE

ALUMINUM C2 1x MAG. AT 75°F, IR REFLECTANCE IMAGE

ALUMINUM C2 1x MAG. AT 84°F, RT-CALIBRATION

ALUMINUM C2 1x MAG. AT 78°F, RT-CALIBRATION

ALUMINUM C2 1x MAG. AT 72°F, RT-CALIBRATION

ALUMINUM C9 (LOW IR PRIMER) IR REFLECTANCE IMAGE

ALUMINUM C9 (LOW IR PRIMER) AT 96°F,
78°F HOT-CALIBRATION

ALUMINUM C9 (LOW IR PRIMER) AT 86°F,
78°F HOT-CALIBRATION

ALUMINUM C9 (LOW IR PRIMER) AT 79°F,
78°F HOT-CALIBRATION

ALUMINUM C9 (LOW IR PRIMER), VISIBLE IMAGE

VISIBLE IMAGE

IR REFLECTANCE IMAGE

IR BLACKBODY IMAGE

SYSTEM FOR DETECTING STRUCTURAL DEFECTS AND FEATURES UTILIZING BLACKBODY SELF-ILLUMINATION

GOVERNMENT CONTRACT

The United States Government has certain rights to this invention pursuant to Contract No. DACA 72-99-C-011 awarded by SERDP.

FIELD OF THE INVENTION

The present invention relates to detection of structural features, and more particularly relates to a system which utilizes blackbody self-illumination to observe defects and other structural features of coated objects such as aircraft components.

BACKGROUND INFORMATION

Aircraft components are subject to constant degradation such as corrosion and cracking caused by environmental and operational conditions. Although the application of coatings, such as paints, reduces corrosion problems substantially, they typically cannot eliminate them entirely. Furthermore, stress experienced during flight can result in damage which a coating of paint cannot mitigate, such as stress defects and cracking. In order to ensure that aircraft are ready for flight, periodic inspections are necessary.

Inspection of aircraft components traditionally includes visual inspection. When visually inspecting aircraft components, the coating used to protect the components becomes an obstacle because it may hide structural defects or features beneath the coating. It is therefore necessary to strip the component assembly or aircraft in question of its paint before a proper visual inspection can be performed. Afterward, a new coating of paint must be applied. This process results in substantial expense in the form of labor and materials, raises environmental concerns, and requires a great amount of time.

Apart from the inefficiency of visual inspection methods, another problem is that visual inspection is not always effective. While a skillful eye may pick up most human-visible defects with a satisfactory degree of consistency, some defects may be very small or lie under the surface of the component. In many cases these defects will go unnoticed by visual inspection regardless of the skill and experience of the observer.

In addition to visual inspection, active thermography techniques have been proposed for inspection of various components. One such technique utilizes a transient heat source to heat the component, followed by detection of a transient heat signature on the surface of the component to determine the presence of anomalies or defects. However, such techniques require specialized equipment and controls to generate the necessary transient heating, and are inefficient because detection of the transient thermal signature can require a significant amount of time.

U.S. Published Patent Application No. US 2004/0026622 A1 discloses a system for imaging coated substrates which utilizes an infrared (IR) light source. The IR light shines on the object and is reflected to a focal plane array. While such a system may be useful for some applications, an IR light source is required and the incident IR radiation must make two passes through the coating. Furthermore, a portion of the incident radiation may reflect off the surface of the coating, thereby obscuring the image of the underlying substrate.

The present invention has been developed in view of the foregoing.

SUMMARY OF THE INVENTION

The present invention utilizes the substantially steady-state temperature of a coated object, in conjunction with an optical detection system, to selectively view defects and features of the object below the coating without the necessity of transient heating or IR illumination and reflectance imaging. The optical detector, such as an IR camera, may be tailored for the wavelengths at which the coating material is substantially transparent, thereby maximizing the viewing clarity of the defects and features under the coating, and distinguishing them from any spurious features on the top surface of the coating. The present system enables the inspection of small or large areas in real time, without requiring complex image acquisition, storage and image processing equipment and software.

An aspect of the present invention is to provide a method of inspecting a coated object. The method includes maintaining substantially steady state blackbody radiation from the object, and detecting structural features of the object under the coating based on the blackbody radiation.

Another aspect of the present invention is to provide a system for inspecting a coated object. The system comprises means for maintaining substantially steady state blackbody radiation from the object, and means for detecting structural features of the object under the coating based on the blackbody radiation.

A further aspect of the present invention is to provide a system for inspecting a coated object comprising a camera structured and arranged to detect structural features of the object under the coating based on substantially steady state blackbody radiation generated from the object.

These and other aspects of the present invention will be more apparent from the following description.

DETAILED DESCRIPTION

Figure 1:
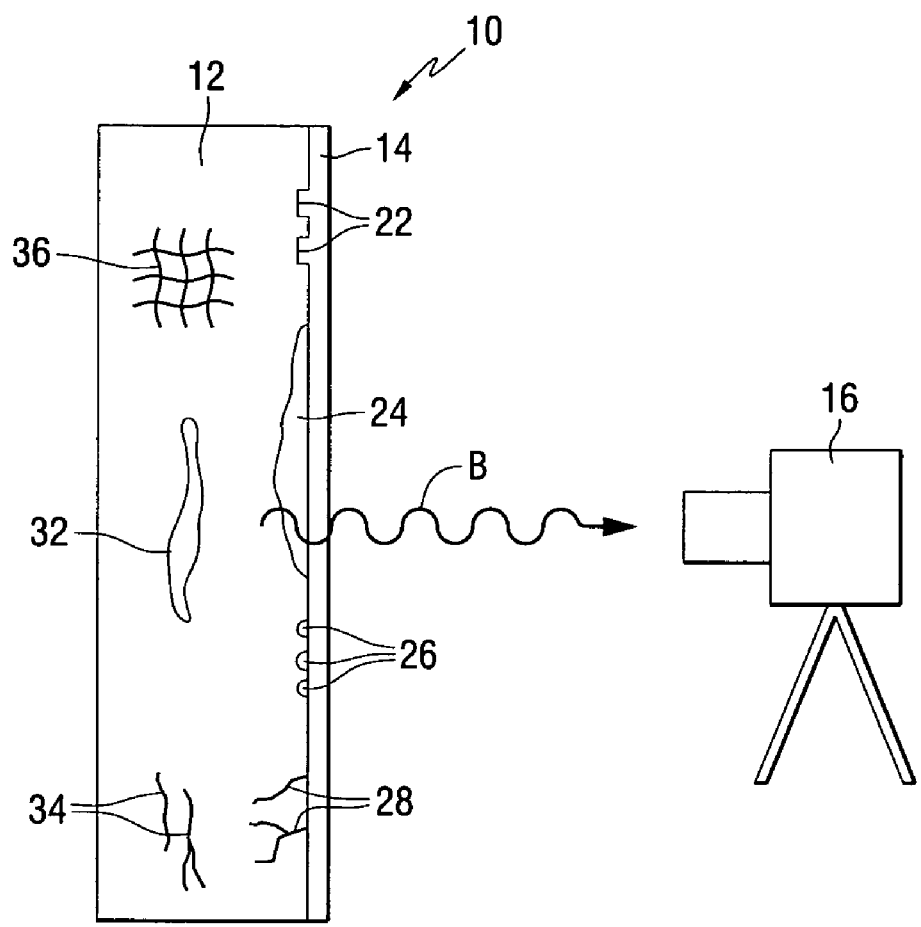
FIG. 1 is a schematic illustration of a system for detecting structural features of a coated object utilizing blackbody self-illumination of the object.

FIG. 1 schematically illustrates a detection system in accordance with an embodiment of the present invention. A coated object 10, such as an aircraft component, composite panel, painted panel, ship hull, ground vehicle, aircraft assembly, aircraft landing gear, metallic substrate, honeycomb bonded assembly or the like, includes a substrate or object 12 at least partially covered with a coating 14 such as paint, composite matrix material or the like. Examples of some specific coatings include coatings manufactured to the following specifications: BMS 10-72; BMS 10-11; BMS-10-79, BMS 10-60; MiL-PRF-23377; MiL-PRF-85582; MiL-PRF-85285 and TT-P-2760. In accordance with the present invention, the object 12 emits blackbody radiation B toward a detector 16 such as an infrared (IR) camera, IR detector or the like.

In accordance with the present invention, the blackbody radiation B from the object 12 is generated in a substantially steady state. As used herein, the term "substantially steady state blackbody radiation" means the radiation naturally generated from the object to be inspected due to its maintenance at a temperature above zero degrees Kelvin, typically at room temperature or a slightly elevated temperature. Steady state blackbody radiation results from maintaining the object or a portion thereof at a substantially uniform temperature, i.e., in the absence of significant thermal gradients throughout the object or portion thereof being inspected.

Since the object 12 is at or near room temperature, it emits a significant amount of substantially steady state infrared (IR) blackbody thermal radiation B. In contrast, the coating 14 may be substantially transparent at some of the wavelengths at which the underlying object emits the blackbody radiation B. Many organic polymers that may be used in the coating 14 are significantly IR-transmissive in certain spectral bands. The blackbody radiation B of the object can penetrate the organic coating 14 covering the object 12 and reveal the surface condition of the object 12 under the coating 14. The radiation B transmitted through the coating 14 is thus used to provide images from the self-illuminated object 12 that reveal any defects such as corrosion, cracks and pits, as well as other structural features under the coating 14. The object 12 to be inspected becomes observable by its own IR radiation B, which is a function of the temperature of the object 12.

As shown in FIG. 1, the object 12 to be inspected may include various types of structural features. The structural features may be located on the surface of the object 12 under the coating 14, or may be located below the surface of the object 12. For example, surface features 22 may be provided on the surface of the object 12 below the coating 14. Examples of surface features 22 include indicia such as alphanumeric symbols, marks, codes, part numbers, bar codes and the like. The object 12 may also include surface defects such as corrosion 24, pits 26, cracks 28, gouges, and other structural defects. As shown in FIG. 1, the object 12 may also include structural features below the surface of the object 12, such as corrosion 32, cracks 34, composite reinforcements 36 and pits 26.

Figure 2:
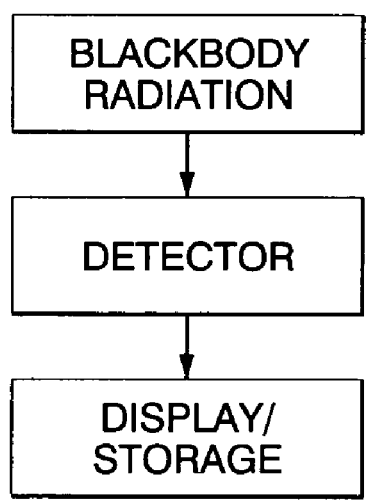
FIG. 2 is a schematic flow diagram illustrating the detection of blackbody radiation from an object to be inspected in accordance with an embodiment of the present invention.

FIG. 2 schematically illustrates a blackbody radiation detection process in accordance with an embodiment of the present invention. Blackbody radiation from an object such as the coated object 10 shown in FIG. 1 is transmitted to a detector such as an IR camera. After detection, an image of the coated object 12, including structural features of the object 10 under the coating 14 may be displayed and/or stored. In addition, the image may be transmitted by any suitable means such as the Internet, wireless, cable or satellite for display and/or storage at any desired location.

In accordance with an embodiment of the present invention, the steady state blackbody radiation B from the object to be inspected may be generated by holding the object at room temperature. The entire object may be maintained at a substantially uniform temperature at or near room temperature. As used herein, the term "room temperature" means the surrounding ambient temperature found in an area such as a testing laboratory, production facility, warehouse, hanger, airstrip, aircraft cabin or ambient exterior temperature. Room temperatures are typically within a range of from about 60 to about 80° F. However, temperatures above or below such a range may exist. For example, in cold environments such as unheated hangers or warehouses in cold regions, the room temperature may be 32° F. or lower. In warm environments such as non-air-conditioned hangers and warehouses in desert or tropical regions, the "room temperature" may be well above 80° F., e.g., up to 100 or 110° F., or even higher.

In accordance with another embodiment of the present invention, the object to be inspected is held at an elevated temperature, e.g., above room temperature, to maintain the substantially steady state blackbody radiation. Such an elevated temperature may be up to about 120° F. or higher, typically in a range of from 80 to about 110° F. The elevated temperature may be maintained by any suitable means, such as exposure to sunlight, heat gun, heat lamp, thermal blanket, hot packs, human contact and the like.

The detector 16 may selectively detect radiation at certain wavelengths at which the coating 14 is substantially transparent. In this manner, the coating 14 does not substantially interfere with the image from the object 12. The detector 16 may include any suitable device such as an IR camera, IR detector, IR focal plane or the like. For example, the camera may be an analog or digital camera, and may record still or video images. Infrared cameras may be used, for example, cameras which detect mid-infrared radiation, e.g., having wavelengths between about 3 and about 5 microns. Such mid-IR wavelengths have been found to produce relatively sharp images with minimal interference from several types of coatings. Other infrared cameras include near-infrared cameras which detect wavelengths between about 0.7 and about 3 microns, and far-infrared cameras which detect wavelengths between about 3 and about 12 microns.

In addition to the camera 16, standard filters and/or polarizers (not shown) may be positioned in the optical path of the blackbody radiation B between the object 12 and the detector 16. Such filters and/or polarizers may remove a portion of the blackbody radiation B having wavelengths at which the coating 14 is non-transparent.

The detector 16 may include a portable or movable camera such as a hand-held camera or a camera that may be mounted on a tripod or the like that can be moved by means of a pan feature and/or a tilt feature.

In accordance with an embodiment of the present invention, the detected image of the object 12, including the detected structural features, may be compared with a reference image. For example, a reference image may be generated from another object similar to the coated object that is known to be substantially free of defects. By comparing a substantially defect-free reference object to the coated object being inspected, manual or automated evaluations may be performed. The reference image used as the standard could be preprogrammed into a database and a comparison made between the reference image and the image created from paint under test. Acceptability criteria could be preprogrammed as well, unacceptable areas could be highlighted in red and acceptable areas in green. Other colors could be selected, as well, such as gray for an area requiring more evaluation.

The following examples are intended to illustrate the various aspects of the present invention and are not intended to limit the scope of the invention.

EXAMPLE 1

Figure 3:
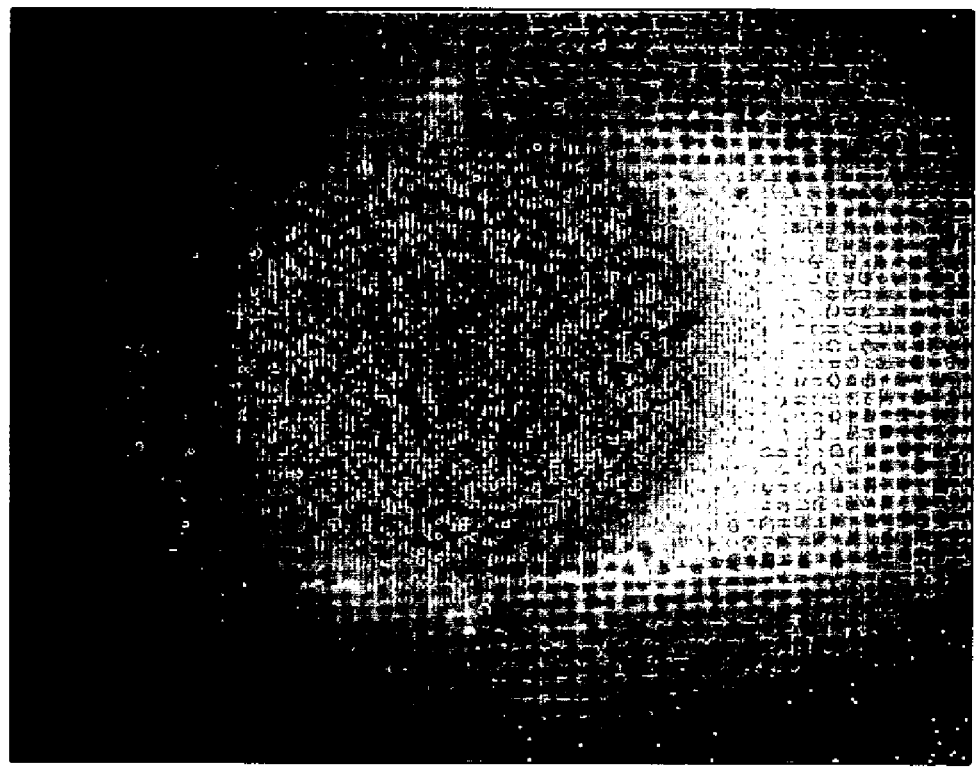
FIGS. 3–26 are blackbody infrared radiation images of coated graphite panels and coated aluminum panels in accordance with various embodiments of the present invention.

As shown in FIG. 3, a painted graphite panel comprising epoxy graphite with an epoxy primer and urethane top coat paint was imaged with a mid-IR camera at the wavelength of 3 to 5 microns. During the imaging process, the panel was held at 89° F. The panel was subjected to a room temperature calibration which involved adjusting pixel intensity to make focal plane uniform and linear within selected room temperature (RT) calibration.

EXAMPLE 2

Figure 4:
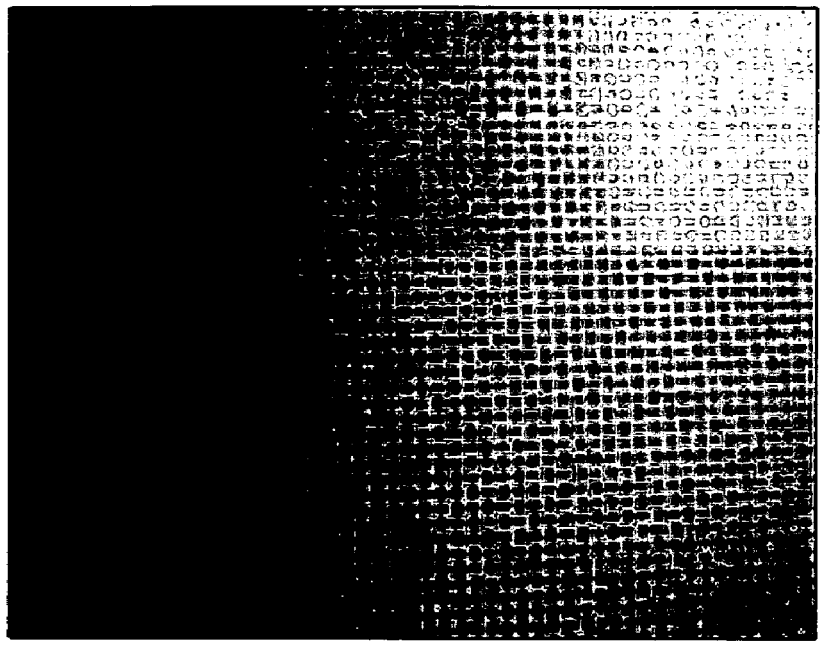

As shown in FIG. 4, a painted graphite panel comprising epoxy graphite and epoxy primer and urethane top coat paint was imaged with a mid-IR camera at a wavelength of 3 to 5 microns with the panel held at a temperature of 90° F. The panel was subjected to hot calibration at a temperature of 84° F. The hot calibration process involved adjusting pixel intensity to make focal plane uniform and linear within selected 84° F. calibration.

EXAMPLE 3

Figure 5:
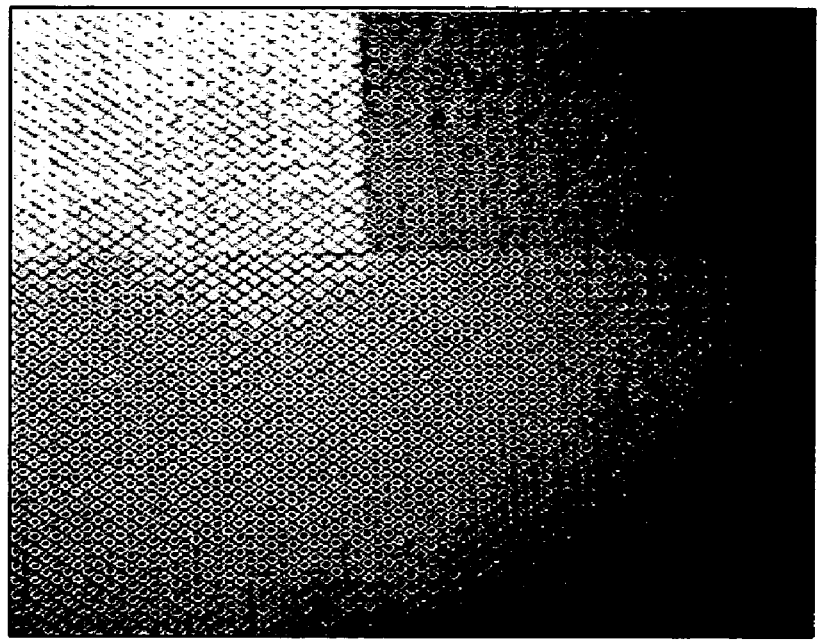

As shown in FIG. 5, a composite panel comprising epoxy graphite and laminated copper fiber painted with epoxy primer and urethane top coat was imaged with a mid-IR camera at a wavelength of 3 to 5 microns, with the panel maintained at a temperature of 90° F. The panel was subjected to hot calibration at 84° F., as described above.

EXAMPLE 4

Figure 6:
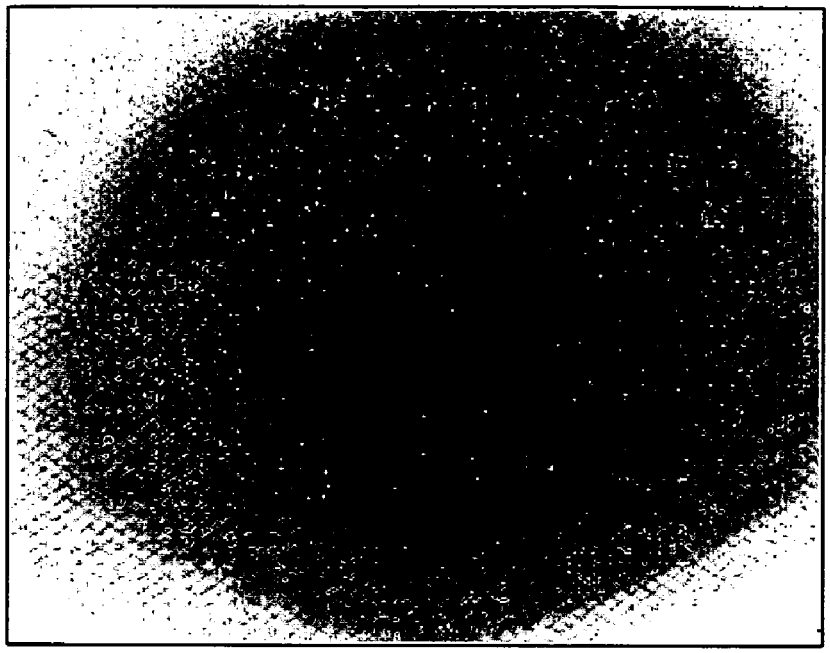

As shown in FIG. 6, a painted graphite and copper fiber panel similar to the panel of Example 3 was imaged at a temperature of 74° F. The panel was subjected to hot calibration at 84° F.

EXAMPLE 5

Figure 7:
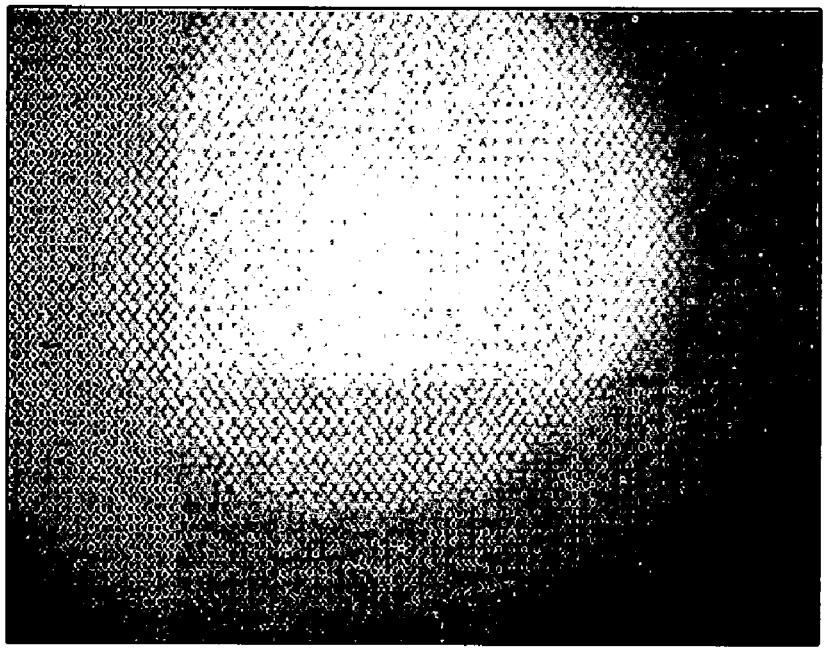

As shown in FIG. 7, a panel comprising epoxy graphite with a laminated copper weave painted with epoxy primer and urethane top coat was imaged at a temperature of 91° F. The panel was subjected to room temperature calibration.

EXAMPLE 6

Figure 8:
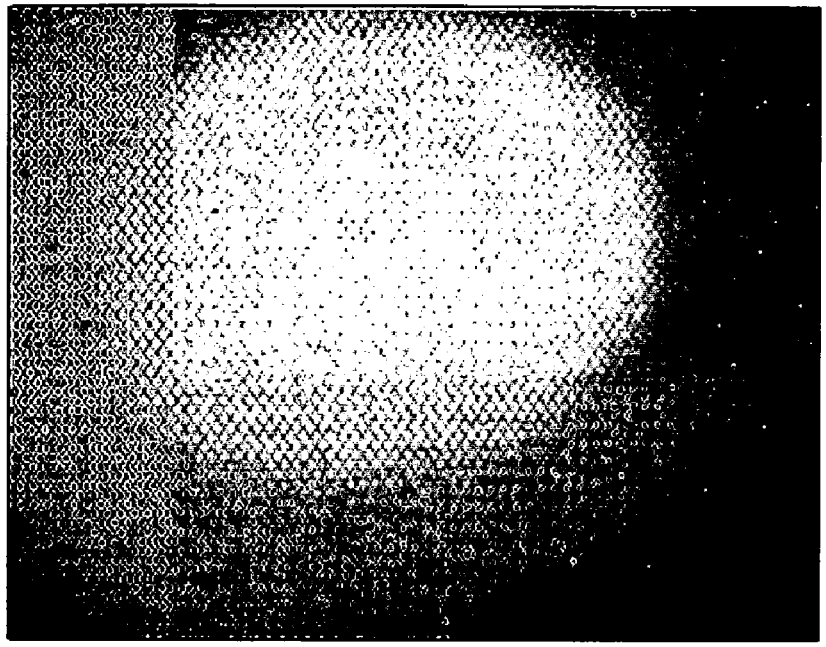

As shown in FIG. 8, a painted graphite and copper weave panel similar to that of Example 5 was imaged at 87° F. after room temperature calibration.

EXAMPLE 7

Figure 9:
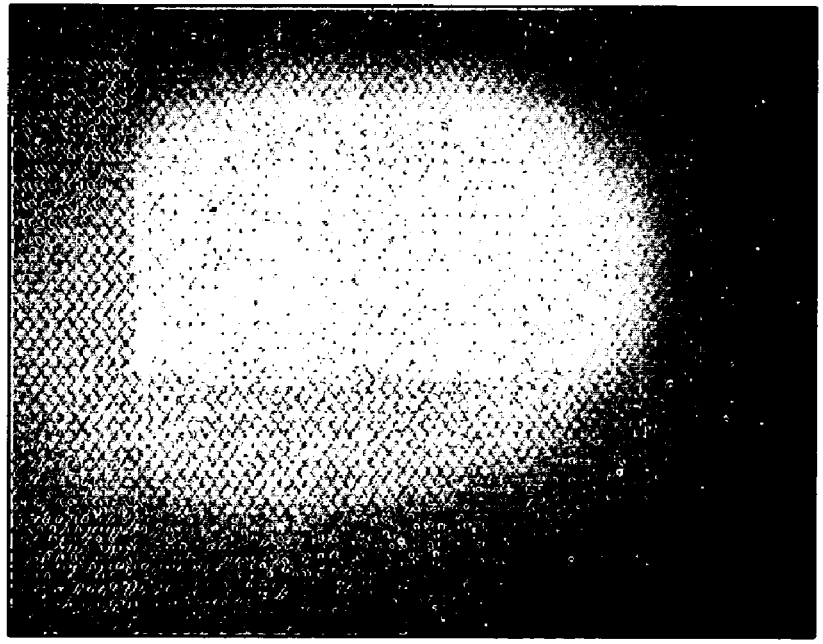

As shown in FIG. 9, a painted graphite and copper weave panel similar to that of Examples 5 and 6 was imaged at 82° F. after room temperature calibration.

EXAMPLE 8

Figure 10:
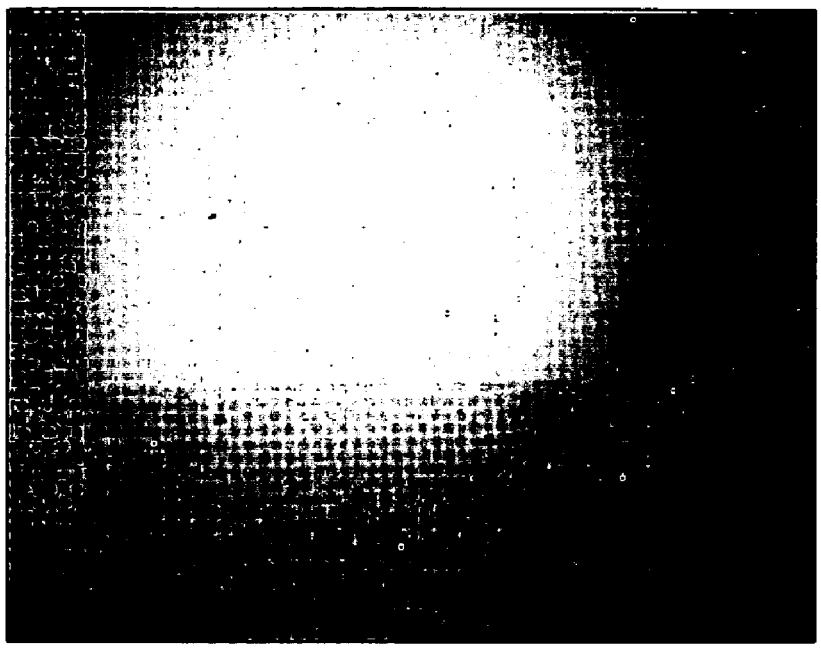

As shown in FIG. 10, an epoxy graphite panel painted with epoxy primer and urethane top coat was imaged at 90° F. after room temperature calibration.

EXAMPLE 9

Figure 11:
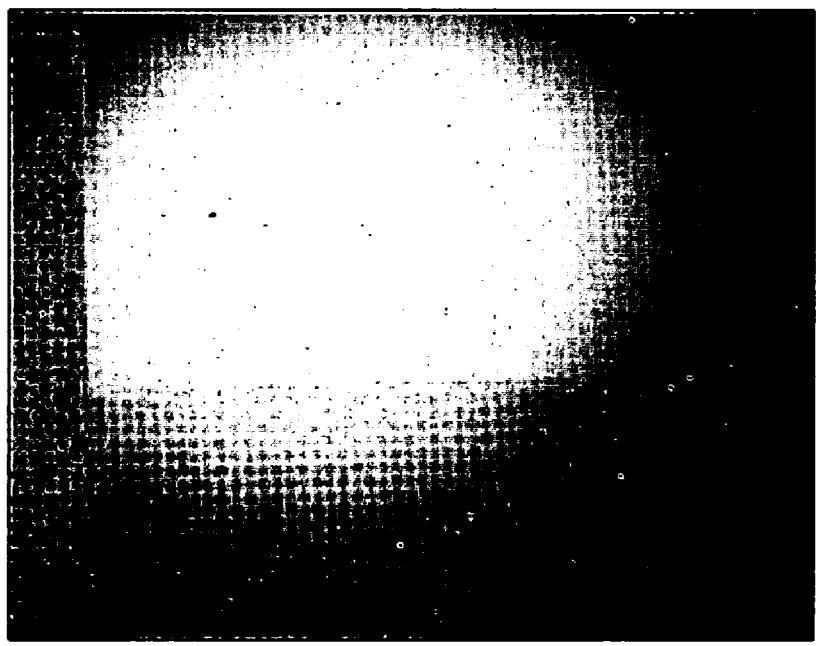

As shown in FIG. 11, a painted graphite panel similar to that of Example 8 was imaged at 86° F. after room temperature calibration.

EXAMPLE 10

Figure 12:
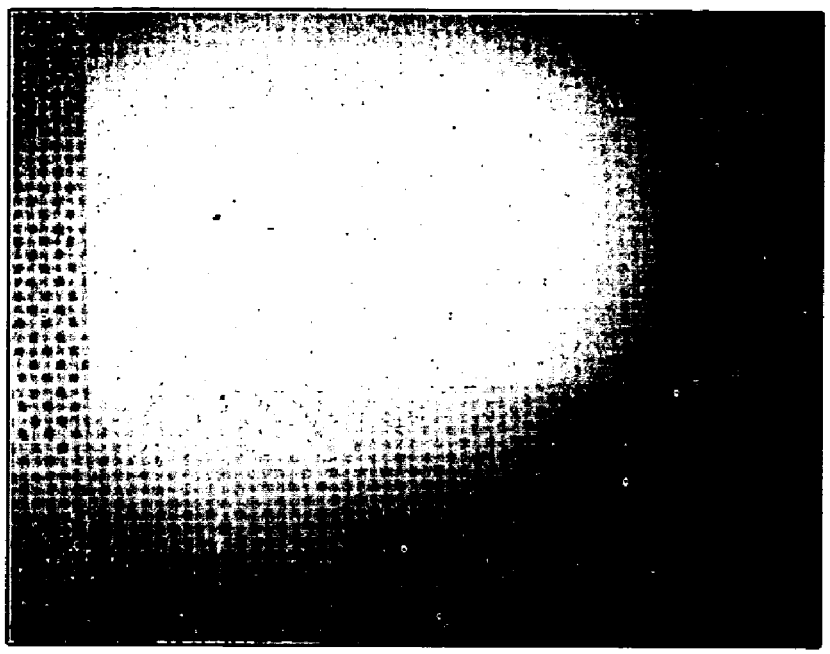

As shown in FIG. 12, a painted graphite panel similar to that of Examples 8 and 9 was imaged at 82° F. after room temperature calibration.

EXAMPLE 11

Figure 13:
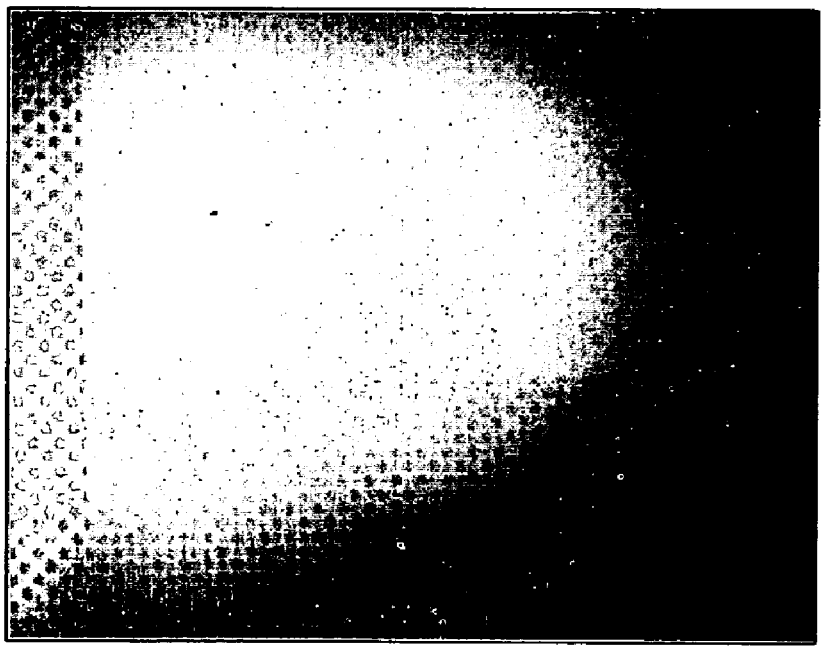

As shown in FIG. 13, a painted graphite panel similar to that of Examples 8–10 was imaged at 78° F. after room temperature calibration.

EXAMPLE 12

Figure 14:
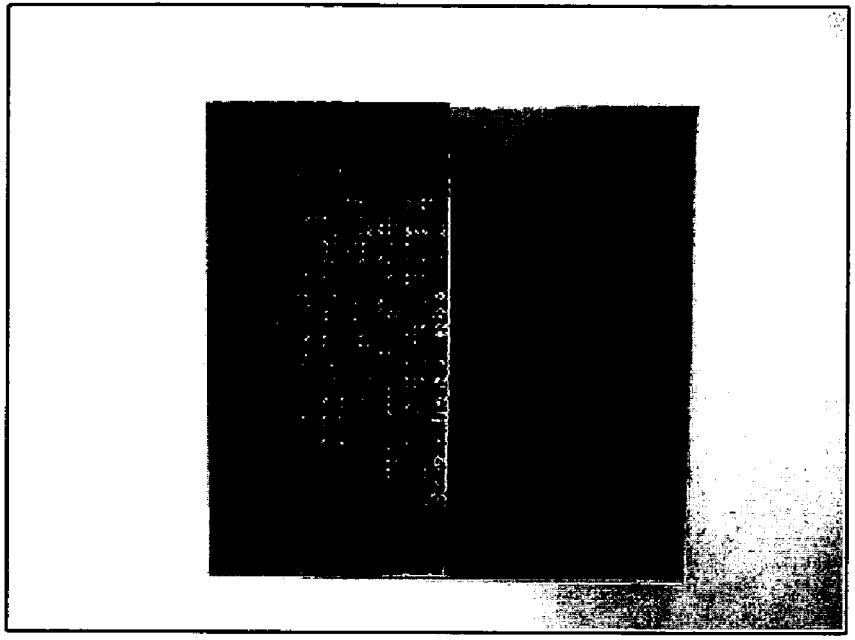

As shown in FIG. 14, a panel comprising epoxy graphite was primed with epoxy primer and painted with epoxy primer and urethane top coat on the right side of the panel. FIG. 14 is a visible image of the painted and primed panel.

EXAMPLE 13

Figure 15:
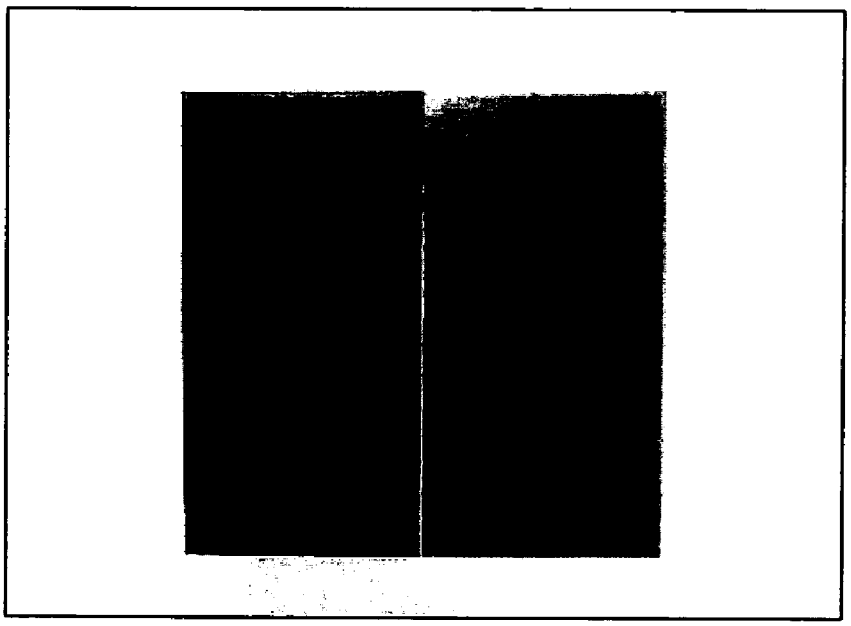

As shown in FIG. 15, a panel comprising graphite with copper weave was primed with epoxy primer in lower right hand side and painted with urethane top coat in upper right of panel. In FIG. 15, the left side of the panel is unprimed and unpainted, while the right side is primed and painted. FIG. 15 is a visual image of the panel.

EXAMPLE 14

Figure 16:
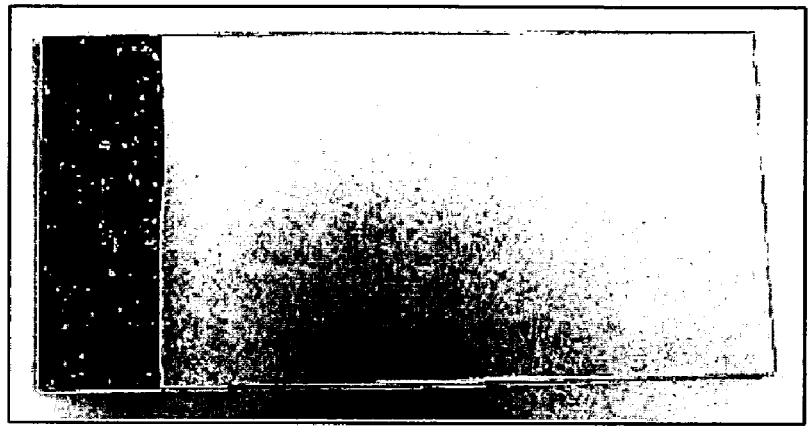

FIG. 16 is a visible image of an aluminum panel comprising a corroded aluminum substrate coated with epoxy primer and urethane top coat.

EXAMPLE 15

Figure 17:

FIG. 17 is an IR reflectance image of the panel of Example 14 at 77° F. The IR reflectanct image was generated by reflecting IR radiation off the aluminum substrate detecting the reflected energy in an IR camera or detector. The corrosion is indicated in dark areas.

EXAMPLE 16

Figure 18:

FIG. 18 is an IR reflectance image of the panel of Example 14 taken 75° F. The corrosion is indicated in dark areas.

EXAMPLE 17

Figure 19:
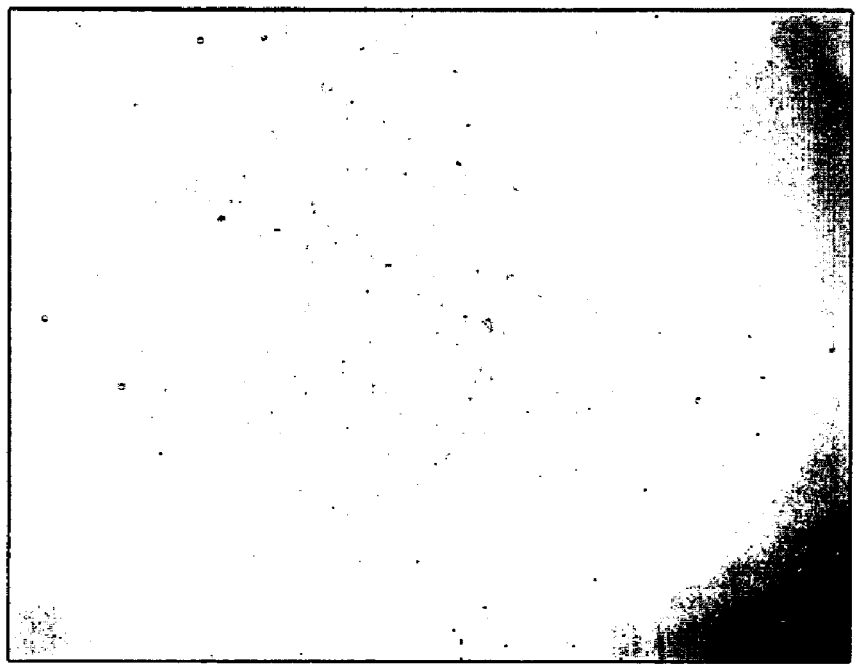

FIG. 19 is a blackbody radiation image made in accordance with the present invention of the coated aluminum panel of Example 14. The panel was maintained at a temperature of 84° F. with a room temperature calibration. The corrosion is indicated in light areas.

EXAMPLE 18

Figure 20:
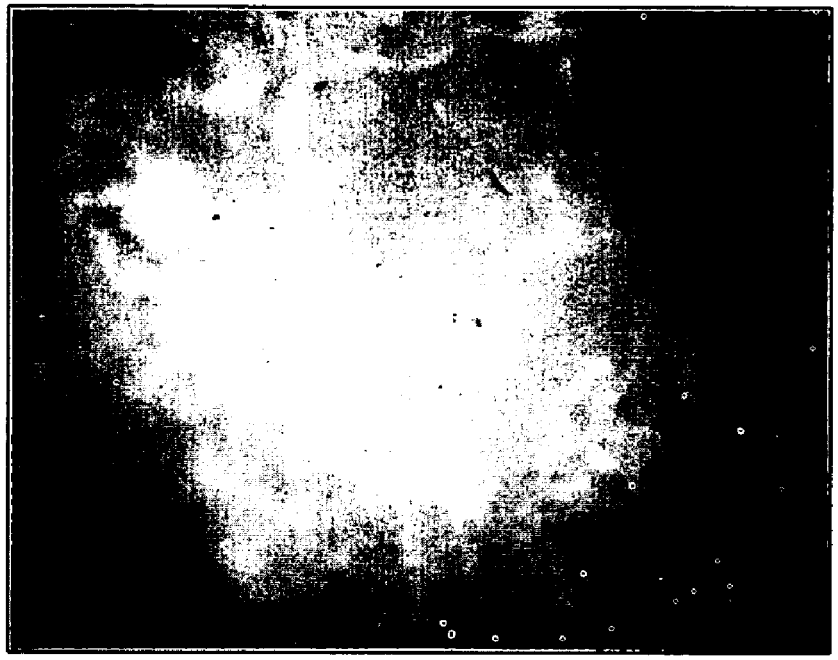

FIG. 20 is a blackbody radiation image made in accordance with the present invention of the coated aluminum panel of Example 14, at 78° F. with a room temperature calibration. The corrosion is indicated in light areas.

EXAMPLE 19

Figure 21:
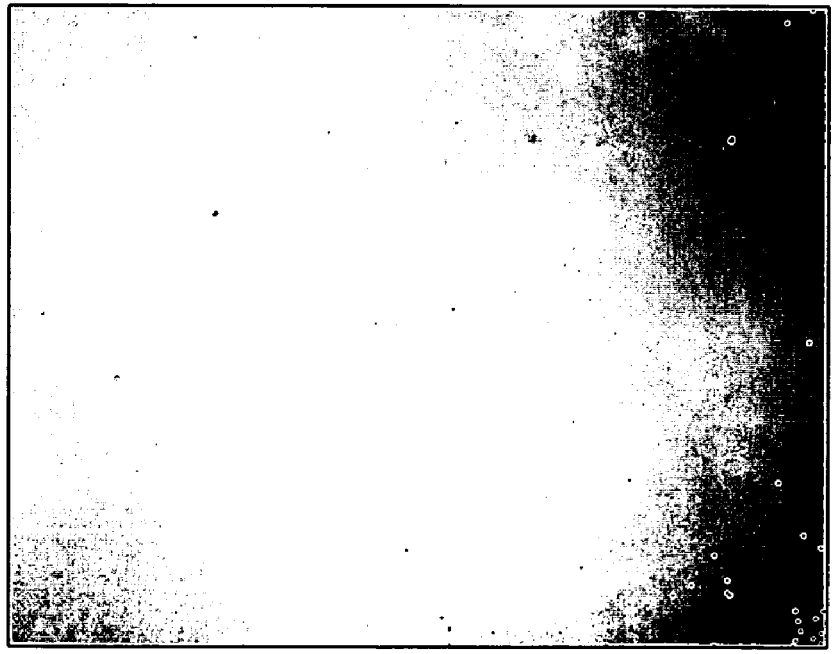

FIG. 21 is a blackbody radiation image made in accordance with the present invention of the coated aluminum panel of Example 14, at 72° F. with a room temperature calibration. The corrosion is indicated in light areas.

EXAMPLE 20

Figure 22:

FIG. 22 is an IR reflectance image of a corroded aluminum panel coated with an epoxy low IR primer and urethane top coat. The IR reflectance image was made by reflecting IR radiation off the coated aluminum substrate and detecting the reflected energy in an IR camera. The corrosion is indicated in dark areas.

EXAMPLE 21

Figure 23:
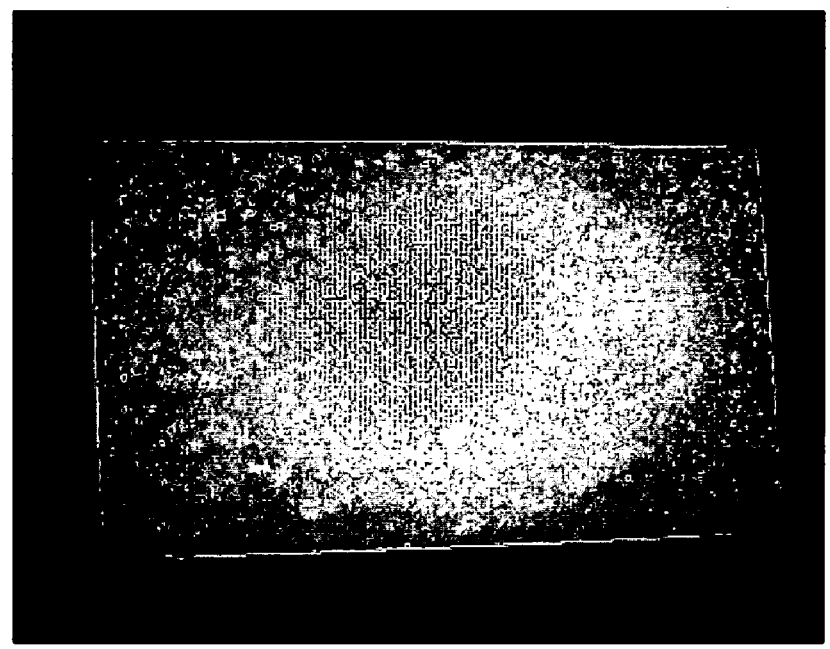

FIG. 23 is a blackbody radiation image produced in accordance with the present invention taken from the same primed and top coated aluminum panel described in Example 20. The blackbody radiation procedure was performed at 96° F. with a 78° F. hot calibration. The corrosion is indicated in light areas.

EXAMPLE 22

Figure 24:
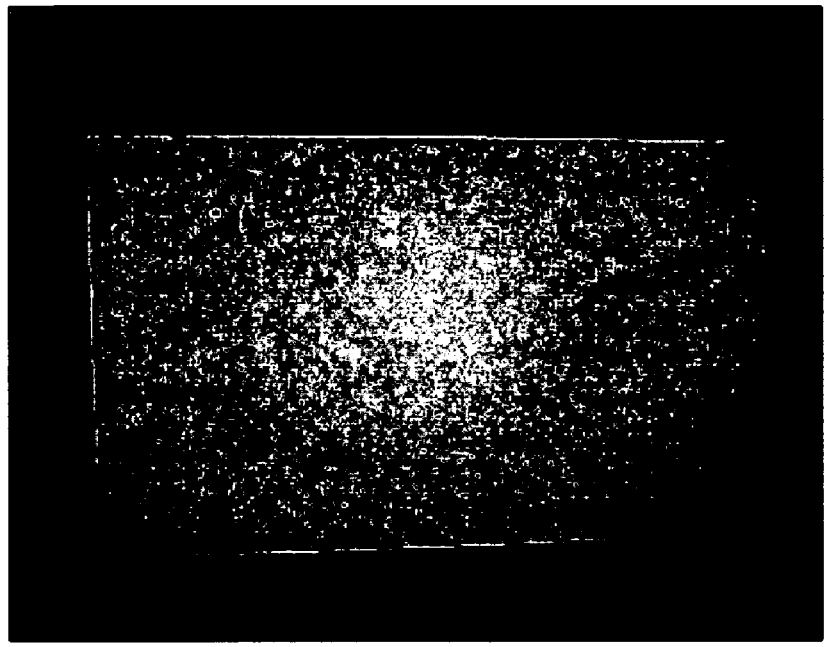

FIG. 24 is a blackbody radiation image produced in accordance with the present invention taken from the same primed and top coated aluminum panel described in Example 20. The blackbody radiation procedure was performed at 86° F. with a 78° F. hot calibration. The corrosion is indicated in light areas.

EXAMPLE 23

Figure 25:
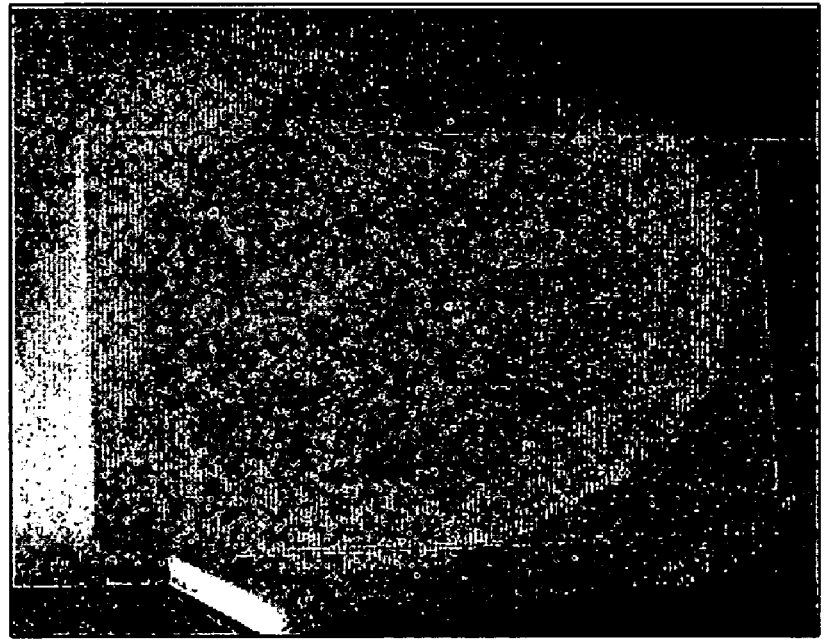

FIG. 25 is a blackbody radiation image produced in accordance with the present invention taken from the same primed and top coated aluminum panel described in Example 20. The blackbody radiation procedure was performed at 79° F. with a 78° F. hot calibration. The corrosion is indicated in light areas.

EXAMPLE 24

Figure 26:
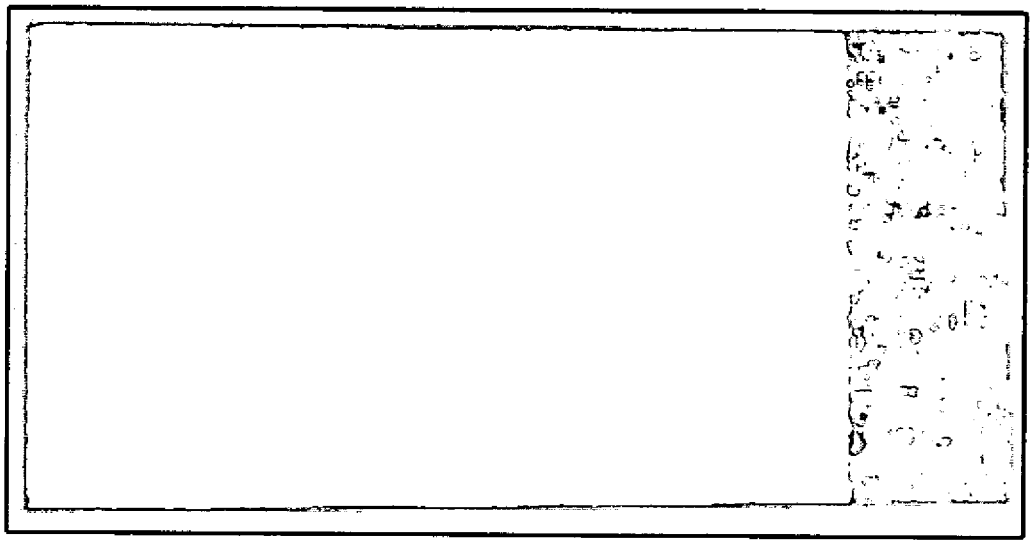

FIG. 26 is a visible image of the primed and top coated aluminum panel of Examples 20 to 23.

The foregoing examples demonstrate that blackbody type IR radiation is capable of passing through coatings and producing an image. External illumination is not required, i.e., the parts are self-illuminating.

EXAMPLE 25

Figure 27A:
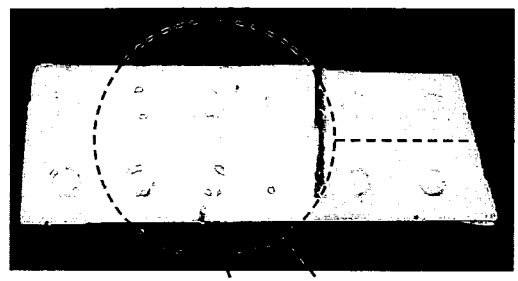
FIGS. 27a–d are visible, IR reflectance, and IR blackbody radiation images of a coated aircraft panel with rivets, showing features of the rivets underneath the coating in accordance with a blackbody self-illumination embodiment of the present invention.
Figure 27B:
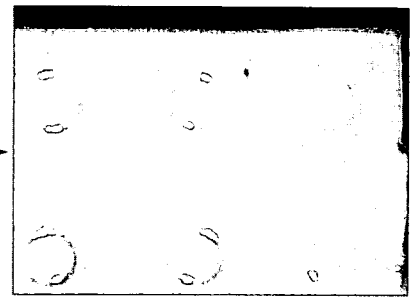
Figure 27C:
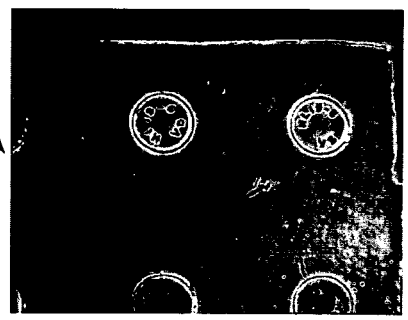
Figure 27D:
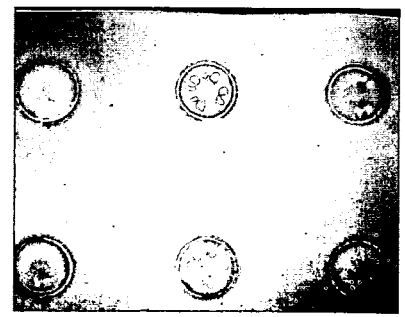

A bolted aluminum aircraft panel was coated with Epoxy primer MIL-PRF-23377TYI and Urethane MIL-PRF-85285TYI paint, as shown in FIG. 27a. It was inspected using visible imaging (FIG. 27b), IR reflectance imaging (FIG. 27c), and IR blackbody imaging (FIG. 27d). The blackbody self-illumination image was made with a mid-IR camera at a wavelength of 3 to 5 microns. During the black body imaging process, the painted aluminum panel was held at a temperature of 85 to 95° F. As shown in FIG. 27d, details of the bolt heads, including alphanumeric symbols, can be seen in the IR blackbody image which are not detectable from the visible image of FIG. 27b.

An advantage of the present blackbody self illumination system is that an independent IR illumination source is not needed. In some cases, an object's IR radiation at ambient temperature may be sufficient to allow imaging of the object through the coating, while in other situations moderate heating of the object to a slightly elevated temperature may be desirable. Such heating can be achieved naturally, e.g., by sunlight, or by a heat gun, thermal blankets, an IR heat lamp, or by other means that produce a substantially steady-state temperature of the object.

Another advantage of the present blackbody system is that the IR radiation only has to make one pass through the coating. This is more efficient compared to IR reflectance techniques, in which IR radiation from an external illuminator must first penetrate the coating, reflect off the substrate or object and pass through the coating again. An additional advantage of the present blackbody method is the reduction or elimination of the coating surface reflection. In the reflectance method, IR energy is reflected off the coating surface partially obscuring the image from the substrate underneath.

Whereas particular embodiments of this invention have been described above for purposes of illustration, it will be evident to those skilled in the art that numerous variations of the details of the present invention may be made without departing from the invention as defined in the appended claims.

The invention claimed is:

1. A method of inspecting a coated object, the method comprising:
    maintaining substantially steady state blackbody radiation from the object; and
    detecting structural features of the object under the coating based on the blackbody radiation.

2. The method of claim 1, wherein the object is held at room temperature to maintain the substantially steady state blackbody radiation.

3. The method of claim 2, wherein the room temperature is from about 32 to about 80° F.

4. The method of claim 1, wherein the object is held at an elevated temperature to maintain the substantially steady state blackbody radiation.

5. The method of claim 4, wherein the elevated temperature is less than about 120° F.

6. The method of claim 4, wherein the elevated temperature is from about 80 to about 110° F.

7. The method of claim 4, wherein the elevated temperature is maintained by exposing the object to sunlight.

8. The method of claim 4, wherein the elevated temperature is maintained by heating the object with a heat gun, a heat lamp and/or a thermal blanket.

9. The method of claim 1, wherein the structural features of the object are detected using an infrared camera.

10. The method of claim 9, wherein the infrared camera detects mid-infrared radiation having wavelengths between about 3 and about 5 microns.

11. The method of claim 9, wherein the infrared camera detects near-infrared radiation having wavelengths between about 0.7 and about 3 microns.

12. The method of claim 9, wherein the infrared camera detects far-infrared radiation having wavelengths between about 3 and about 12 microns.

13. The method of claim 1, wherein the structural features of the object are detected using an imaging device which detects radiation having at least one wavelength at which the coating is substantially transparent.

14. The method of claim 1, wherein the structural features of the object are detected using a movable camera.

15. The method of claim 14, wherein the movable camera is a hand-held camera.

16. The method of claim 14, wherein the movable camera is mounted at a single location during the detection, and includes a pan feature and/or a tilt feature.

17. The method of claim 1, wherein the structural features of the object are detected using a camera and a filter located in an optical path between the object and the camera.

18. The method of claim 17, wherein the filter removes a portion of the blackbody radiation having wavelengths at which the coating is non-transparent.

19. The method of claim 1, wherein the structural features of the object are detected using a camera and a polarizer located in an optical path between the object and the camera.

20. The method of claim 1, wherein the structural features comprise defects.

21. The method of claim 1, wherein the defects are on a surface of the object under the coating.

22. The method of claim 21, wherein the surface defects comprise corrosion, cracks, pits and/or gouges.

23. The method of claim 20, wherein the defects are under a surface of the object.

24. The method of claim 23, wherein the defects comprise corrosion, cracks and/or voids.

25. The method of claim 1, wherein the structural features comprise surface features on a surface of the object under the coating.

26. The method of claim 25, wherein the surface features comprise indicia.

27. The method of claim 26, wherein the indicia comprises alphanumeric symbols, marks or codes.

28. The method of claim 1, wherein the structural features comprise features under a surface of the object.

29. The method of claim 28, wherein the features comprise composite reinforcements and/or composite matrix materials.

30. The method of claim 1, wherein the object comprises an aircraft component.

31. The method of claim 1, wherein the coating comprises paint, a composite matrix material, primer, top coat and/or intermediate coatings.

32. The method of claim 1, further comprising displaying an image of the object including the detected structural features.

33. The method of claim 1, further comprising storing an image of the object including the detected structural features.

34. The method of claim 1, further comprising transmitting an image of the object including the detected structural features.

35. The method of claim 34, wherein the image is transmitted over the internet.

36. The method of claim 1, further comprising comparing an image of the object including the detected structural features with a reference image.

37. The method of claim 35, wherein the reference image is generated from another object similar to the coated object that is substantially free of defects.

38. A system for inspecting a coated object comprising:
means for maintaining substantially steady state blackbody radiation from the object; and
means for detecting structural features of the object under the coating based on the blackbody radiation.

39. A system for inspecting a coated object comprising a camera structured and arranged to detect structural features of the object under the coating based on substantially steady state blackbody radiation generated from the object.

* * * * *